(12) United States Patent
Liu

(10) Patent No.: US 9,448,269 B2
(45) Date of Patent: Sep. 20, 2016

(54) ELECTROSTATIC DETECTING CIRCUIT AND METHOD THEREOF

(71) Applicant: Raydium Semiconductor Corporation, Hsinchu (TW)

(72) Inventor: Cheng-Chin Liu, Taichung (TW)

(73) Assignee: Raydium Semiconductor Corporation, Hsinchu County (TW)

( * ) Notice: Subject to any disclaimer, the term of this patent is extended or adjusted under 35 U.S.C. 154(b) by 201 days.

(21) Appl. No.: 14/286,663

(22) Filed: May 23, 2014

(65) Prior Publication Data

US 2014/0347061 A1 Nov. 27, 2014

(30) Foreign Application Priority Data

May 24, 2013 (TW) .............................. 102118347 A

(51) Int. Cl.
| | |
|---|---|
| G01R 29/12 | (2006.01) |
| G01R 31/00 | (2006.01) |
| G01R 29/24 | (2006.01) |
| G01N 27/60 | (2006.01) |
| G01R 5/28 | (2006.01) |
| G01R 31/12 | (2006.01) |
| G01R 19/00 | (2006.01) |
| G01R 15/16 | (2006.01) |

(52) U.S. Cl.
CPC ............ *G01R 31/002* (2013.01); *G01N 27/60* (2013.01); *G01R 5/28* (2013.01); *G01R 29/12* (2013.01); *G01R 29/24* (2013.01); *G01R 31/12* (2013.01); *G01R 15/165* (2013.01); *G01R 19/0023* (2013.01)

(58) Field of Classification Search
CPC .... G01R 31/002; G01R 31/12; G01R 29/08; G01R 29/12; G01R 29/24; G01R 5/28; G01R 15/165; G01R 19/0023; G01N 27/60
USPC .......................................................... 324/457
See application file for complete search history.

(56) References Cited

U.S. PATENT DOCUMENTS

| | | | | |
|---|---|---|---|---|
| 4,139,813 | A * | 2/1979 | Shaffer .............. | G01R 1/06766 324/457 |
| 4,947,468 | A * | 8/1990 | Nelson .................. | G01R 29/24 324/453 |
| 5,519,384 | A * | 5/1996 | Chanudet ............. | G01R 31/026 324/509 |
| 7,138,804 | B2 * | 11/2006 | Ker ...................... | G01R 31/002 324/452 |
| 7,928,753 | B2 * | 4/2011 | Fefer .................... | G01R 31/002 324/762.01 |
| 7,982,499 | B2 * | 7/2011 | Ng ........................ | G01R 31/002 326/27 |
| 8,183,664 | B2 * | 5/2012 | Jung .................... | G01R 31/002 257/510 |

* cited by examiner

*Primary Examiner* — Hoai-An D Nguyen

(57) ABSTRACT

An electronic detecting circuit includes at least one electrostatic protective module, at least one detection module, and a microprocessor controller module. The at least one detection module is respectively connected to the at least one electrostatic protective module, and the at least one detection module generates a driving record signal according to a driving state of the at least one electrostatic protective module. The microprocessor controller module is coupled with the at least one detection module, wherein the microprocessor controller module records the driving record signal when the at least one detection module transmits the driving record signal to the microprocessor controller module.

14 Claims, 4 Drawing Sheets

ELECTROSTATIC DETECTING CIRCUIT AND METHOD THEREOF

BACKGROUND OF THE INVENTION

1. Field of the Invention

The present invention generally relates to a protective circuit with protective electrostatic recording capabilities; particularly, the present invention relates to an electrostatic detection module for increasing electrostatic protection of displays and having a recording mechanism.

2. Description of the Related Art

In a conventional circuit, researchers place ESD components (Electrostatic Discharge components) to protect circuit chips in order to prevent damage to the circuit chips from electrostatic attacks. However, in actual conditions, researchers are only able to determine the placement location and protection levels of the electrostatic components from experience, and are not able to predict and record where the electrostatic current is hidden.

It should be noted that researchers improve on the electrostatic protection mechanism only after the electronic component and circuit chip has been damaged by an electrostatic attack. In other words, present electrical circuits lacks good electrostatic protection recording mechanisms and consequently are not able to provide good protection for circuits. In addition, out of precaution, researchers typically place vast amounts of ESD components to protect the electrical circuits. However, not all of the ESD components are necessary and thus help to incur unnecessary costs.

Accordingly to the above mentioned problems, designs allowing the recordation of electrostatic protection positions in order to increase circuit protection capabilities have currently become a pressing issue.

SUMMARY OF THE INVENTION

It is an object of the present invention to provide an electrostatic detecting circuit having a protection recording mechanism to increase protection capabilities.

It is another object of the present invention to provide an electrostatic protection circuit having a detection module to record electrostatic driving state.

It is yet another object of the present invention to provide an electrostatic protection circuit with readable electrostatic protection status to build an electrostatic protection distribution map.

According to an embodiment of the present invention, the electrostatic detecting circuit includes at least one electrostatic protective module, at least one detection module, and a microprocessor controller module, wherein at least one detection module is respectively connected to at least one electrostatic protective module, and at least one detection module generates a driving record signal according to driving status of at least one electrostatic protective module. The microprocessor controller module is coupled to at least one detection module, wherein the microprocessor controller module records the driving record signal when the at least one detection module transmits the driving record signal to the microprocessor controller module.

According to another embodiment of the present invention is an electrostatic detecting method. The electrostatic detecting method includes generating by at least one detection module a driving record signal according to driving status of at least one electrostatic protective module; and through the at least one detection module, when transmitting the driving record signal to a microprocessor controller module, recording the driving record signal with the microprocessor controller module.

In comparison to the prior art, the present invention of the electrostatic protection circuit and the electrostatic detecting method detects driving status of the electrostatic protective module through the detection module and outputs driving record signal according to the driving status. The circuit path and protection positions of the protection circuit are then recorded. It should be noted that the microprocessor controller module can read the driving record signal to build an electrostatic protection diagram. In addition, within the electrostatic protection diagram, the electrostatic protection circuit can adjust certain blocks of the protective components of the electronic component to selectively switch off the protective components or adjust protection levels thereof in order to accomplish the effect of detecting electrostatic protection and authentication.

The following specification and diagrams are provided to facilitate better understanding of the present invention.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

According to an embodiment of the present invention of an electrostatic detecting circuit, the electrostatic detecting circuit can record electrostatic protection positions. In the present embodiment, the electrostatic detecting circuit is an electrostatic detecting circuit of display devices; however, the electrostatic detecting circuit is not limited to display devices. In other different embodiments, the electrostatic detecting circuit may be applicable to computers, electronic mobile devices, media players, or any other electronic devices without any particular restrictions.

Figure 1:
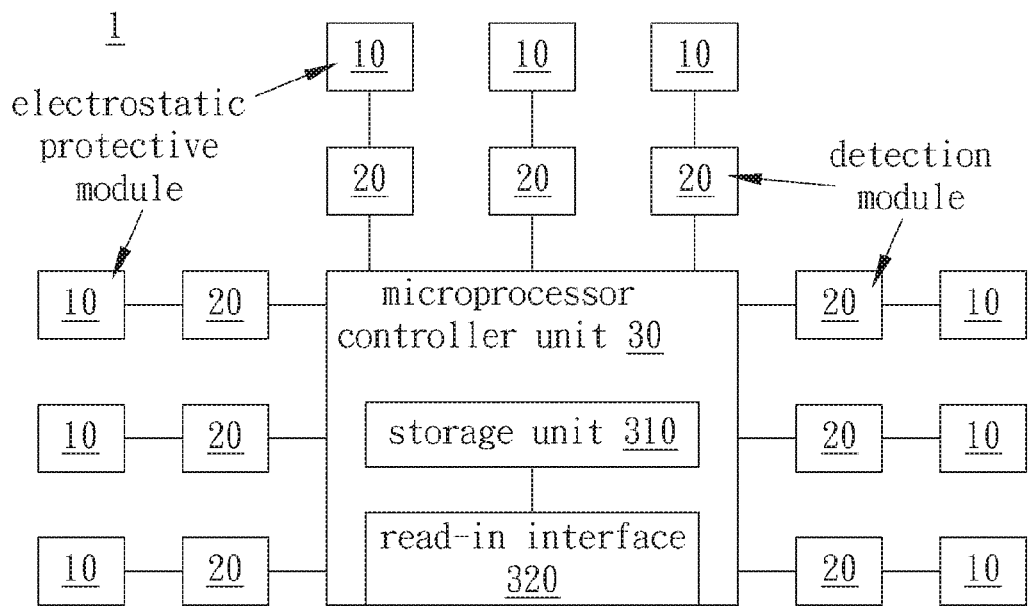
FIG. 1 is a view of an embodiment of the electrostatic detecting (protection) circuit of the present invention.

Please refer to FIG. 1. FIG. 1 is an illustration of an embodiment of the electrostatic protection circuit of the present invention. As shown in FIG. 1, the electrostatic detecting circuit 1 includes at least one electrostatic protective module 10, at least one detection module 20, and a microprocessor controller module 30. In the present embodiment, the detection module(s) 20 are respectively connected to the electrostatic protective module(s) 10, and the microprocessor controller module 30 is coupled to the detection module 20. In actual circumstances, the detection module 20 generates a driving record signal according to driving status of the electrostatic protective module 20, wherein the microprocessor controller module 30 records or logs the driving record signal when the detection module 20 transmits the driving record signal to the microprocessor controller module 30.

It should be noted that the electrostatic detecting circuit 1 is a circuit of a display, and the microprocessor controller module 30 is a timing controller module. However, the electrostatic detecting circuit 1 and the microprocessor controller module 30 are not necessarily restricted to these embodiments.

Figure 2:
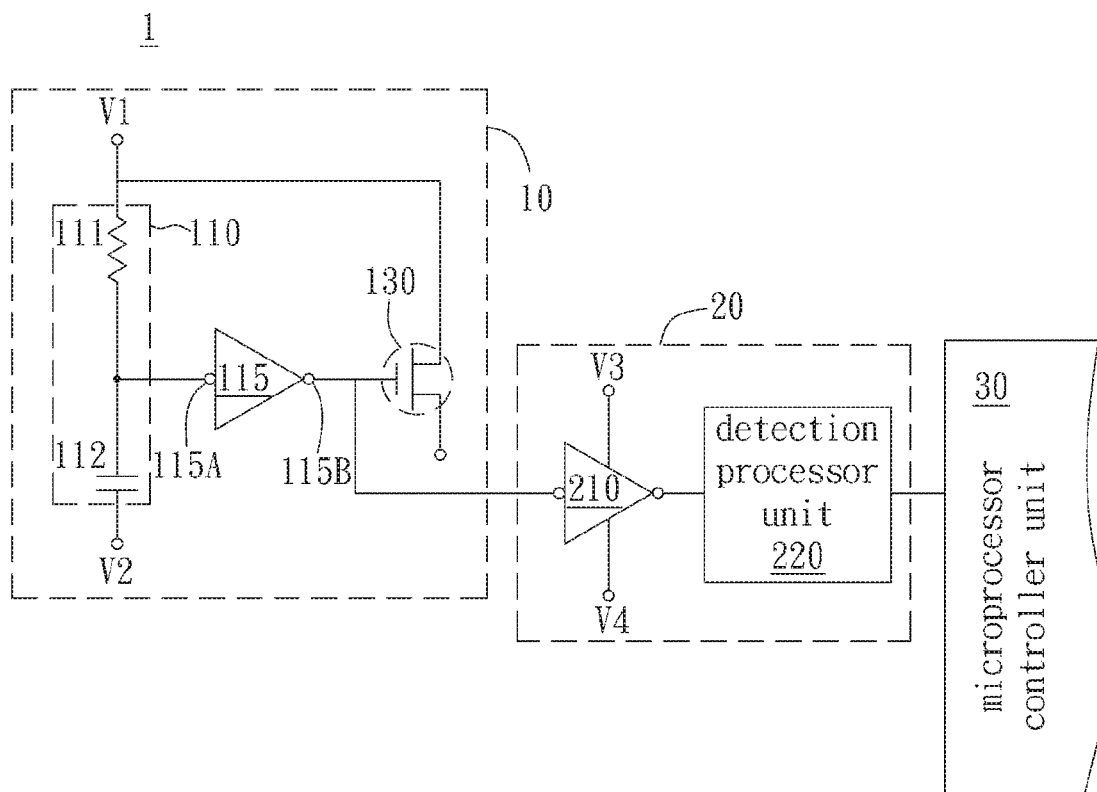
FIG. 2 is a view of an embodiment of the electrostatic detecting (protection) circuit of the present invention.

The following are detailed explanations of FIG. 2 on how the electrostatic protection is recorded and how the electrostatic protective capabilities are increased.

Please refer to FIG. 2. FIG. 2 is an illustration of an embodiment of the electrostatic detecting circuit of the present invention. As shown in FIG. 2, the electrostatic detection module 10 includes a delay circuit 110, an inverter 115, and a bypass processing unit 130, wherein the delay circuit 110 includes a protective resistor 111 and a protective capacitor 112. The inverter 115 has an inverter input terminal 115A and an inverter output terminal 115B.

In addition, the electrostatic detection module 10 has a first voltage V1 and a second voltage V2. The first voltage V1 can be a high voltage gate (VGH), an analog duty voltage (AVDD), a digital duty voltage (DVDD), or an analog voltage source (VDDA). The second voltage V2 can be a low voltage gate (VGL), an analog ground voltage (AVSS), a digital ground voltage (DVSS), or a digital ground voltage source (VSSA). The voltage of the first voltage V1 and the second voltage V2 is set according to actual circumstances and not particularly limited or restricted by the described embodiment.

It should be noted that the detection module 20 generates the driving record signal according to whether the protection state of the electrostatic protective module 10 has changed from stop protection state to drive protection state. In actual circumstances, the detection module 20 is connected to the inverter output terminal 115B of the inverter 115, and the detection module 20 has a detection inverter 210 and a detection processor unit 220. In addition, the detection inverter 210 has a third voltage V3 and a fourth voltage V4, wherein the third voltage V3 can be a digital duty voltage (DVDD) and the fourth voltage V4 can be a digital ground voltage (DVSS).

In the present embodiment, the detection inverter 210 is a JK inverter. However, the detection inverter 210 is not limited to being a JK inverter. When the electrostatic protective module 10 is in the drive protection state, the inverter output terminal 115B generates the electrostatic surge signal to the detection inverter 210 of the detection module 20. The detection inverter 210 of the detection module 20 transforms the electrostatic surge signal to the driving record signal, wherein the driving record signal is a direct current voltage signal. In addition, the detection processor unit 220 helps process the direct current voltage signal and transmits it to the microprocessor controller module. In further discussion, in other embodiments, the detection module 20 may not have the detection inverter 210. Instead, the detection module 20 may have a unit device capable of transforming the electrostatic surge signal into the driving record signal. However, the detection module 20 is not limited or restricted to these embodiments.

In the present embodiment, the driving record signal is a digital logic signal, wherein the microprocessor controller module 30 stores and records the digital logic signal. For instance, when the electrostatic protection status of the electrostatic protective module 10 remains in the stop protection state, the digital logic signal is 0. When the electrostatic protection status of the electrostatic protective module 10 changes from the stop protection state to the drive protection state, the digital logic signal is 1.

In actual circumstances, the microprocessor controller module 30 is able to record and read the driving record signal. As shown in FIG. 1, the microprocessor controller module 30 includes a storage unit 310 and a read-in interface 320, wherein the read-in interface 320 is connected to the storage unit 310. It should be noted that the storage unit 310 stores the driving record signal, and the read-in interface 320 acts as a transmission interface for the driving record signal. Research personnel may read the driving record signal through the read-in interface 320 in order to confirm which electrostatic protective modules 10 have electrostatic protection.

Figure 3:
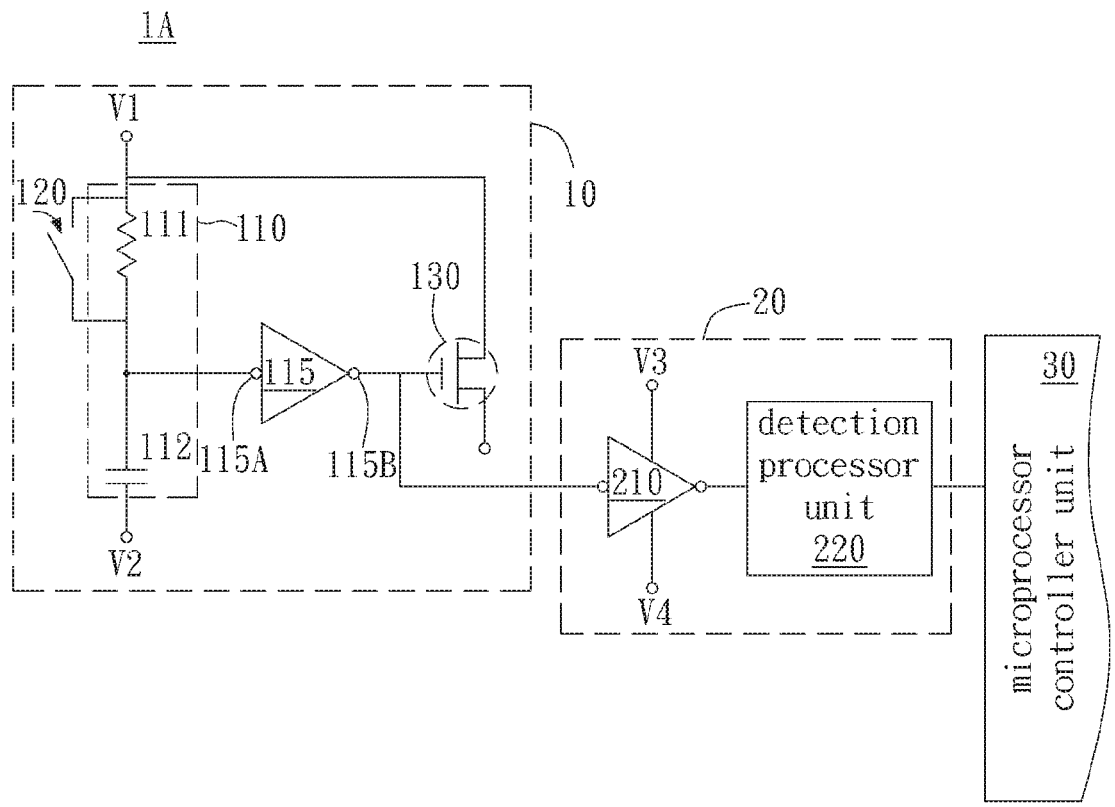
FIG. 3 is a view of another embodiment of the electrostatic detecting (protection) circuit.

Please refer to FIG. 3 of another embodiment of the electrostatic detecting circuit of the present invention. As shown in FIG. 3, the protective module 10A of the electrostatic detecting circuit 1A further includes a control switch 120, wherein the control switch 120 is connected to a protective resistor 111. In actual circumstances, when the control switch 120 is turned on, the protective module 10A stops the driving protection. In other words, the electrostatic detecting circuit 1A may confirm, through the driving protection signal recorded by the microprocessor controller module 30, the electrostatic protective modules 10A which are not driving protection in order to turn off the electrostatic protective module 10A. In actual use, after the electrostatic protective module 10A is turned off, the protective effect of the electrostatic protection of the electrostatic protective module 10A is greater than the protective effect of the electrostatic protective module 10A when originally turned on.

Figure 4:
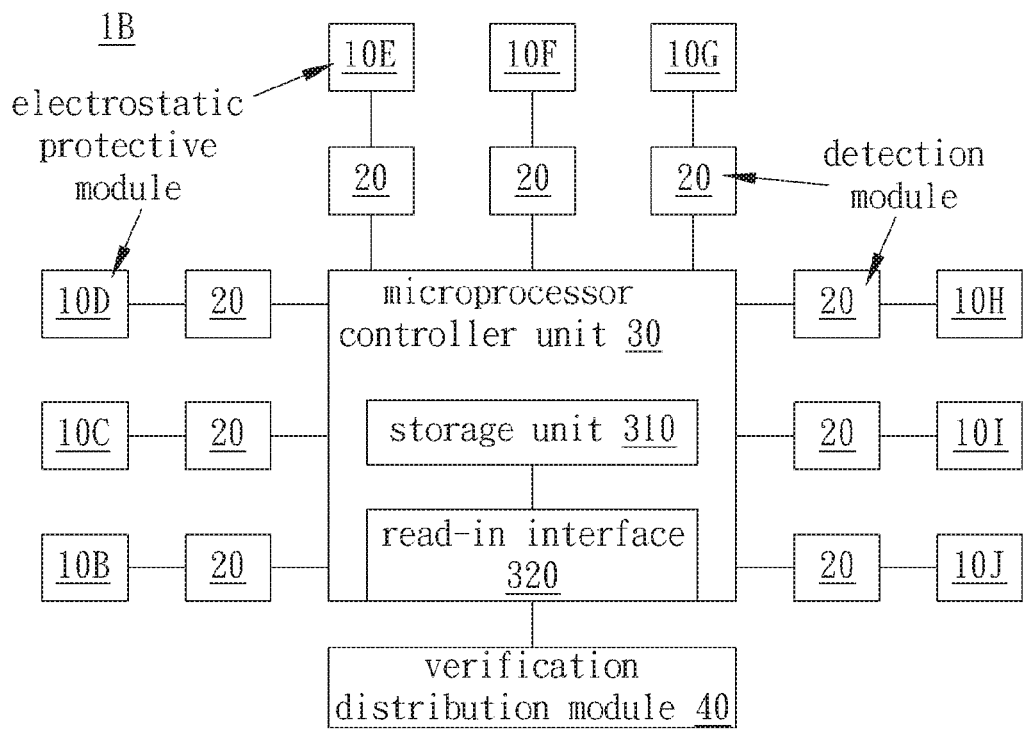
FIG. 4 is a view of another embodiment of the electrostatic detecting (protection) circuit.

Please refer to FIG. 4 of another embodiment of the electrostatic detecting circuit of the present invention. As shown in FIG. 4, the electrostatic detecting circuit 1B further includes a verification distribution module 40 and those electrostatic protective modules 10B~10J, wherein the verification distribution module 40 is connected to the read-in interface 320 of the microprocessor controller module 30. It should be noted that those electrostatic protective modules 10B~10J are the same as the electrostatic protective module 10A of FIG. 3 (except with the use of different numbering labels). In addition, the verification distribution module 40 reads the position and driving record signal of each of the electrostatic protective modules 10B~10J to determine the protection verification distribution map. For instance, if the microprocessor controller module 30 confirms according to the driving record signal that the electrostatic protective module 10B and 10C are not being driven, in actual circumstances the researcher may manually control—or control through microprocessor controller module 30—the on/off of the control switch 120 of the electrostatic protective modules 10B and 100 to turn off the electrostatic protection or adjust the electrostatic protection levels of the electrostatic protective modules 10B and 10C. In this manner, the electrostatic detecting circuit 1B will have better electrostatic protection effects.

In the present embodiment, the electrostatic detecting circuit 1B builds the protection verification distribution map through those driving record signals. The electrostatic detecting circuit 1B can then determine whether to turn on or off the control switches and is able to adjust the electrostatic protection levels of those electrostatic protective modules 10B~10J. In actual circumstances, the electrostatic voltage affects the electrostatic detecting circuit 1B at a relatively lower voltage (2 kV, 4 kV or other voltages). The electrostatic detecting circuit 1B can perform adjustments according to how much the electrostatic protective modules 10B~10J can withstand the electrostatic effect, and in turn improve the electrostatic current path while increasing the electrostatic protection capabilities.

Figure 5:
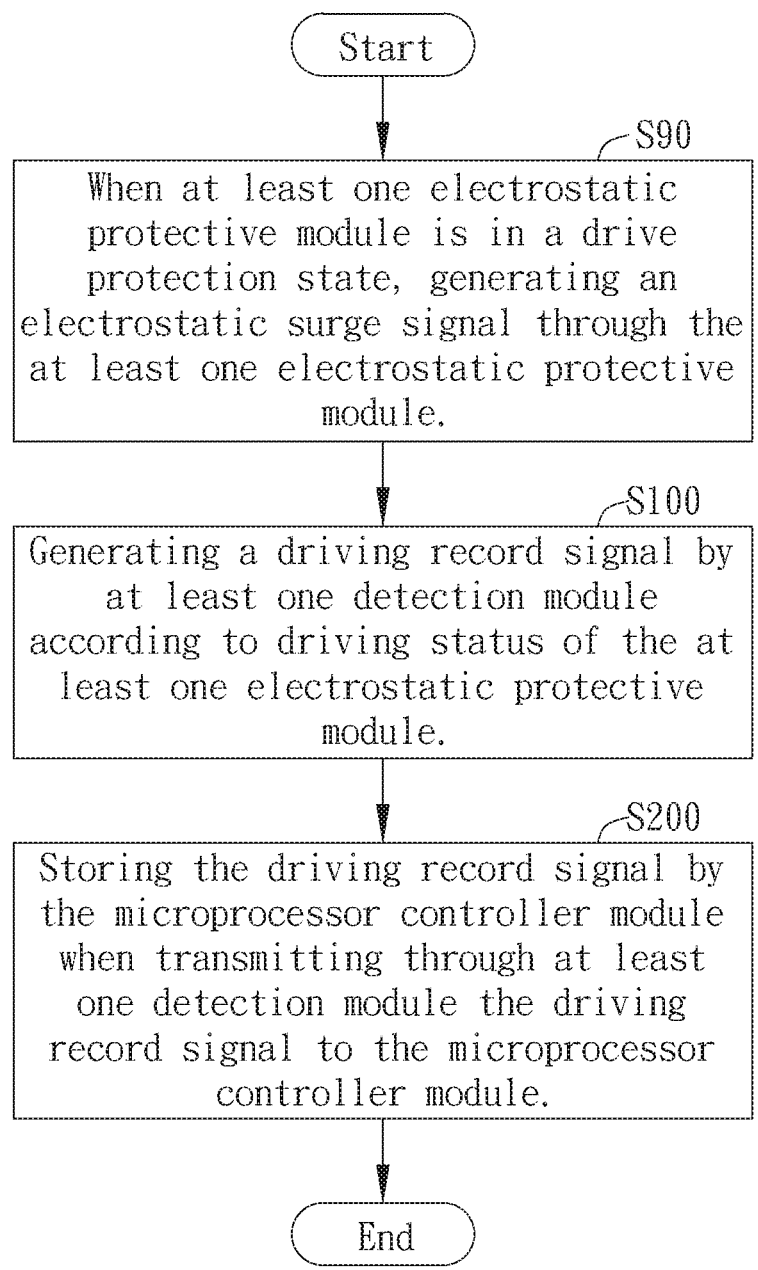
FIG. 5 is a flowchart diagram of an electrostatic detecting method of the present invention.

Please refer to FIG. 5 of a flowchart of an electrostatic detecting method of the present invention. As shown in FIG. 5, the electrostatic detecting method includes the following steps: step S90, when the at least one electrostatic protective module is in a drive protection state, generating an electrostatic surge signal through at least one electrostatic protective module; step S100, according to driving state of at least one electrostatic protective module, generating by at least one detection module a driving record signal; and step 200, recording the driving record signal by the microprocessor controller module when the at least one detection module transmits the driving record signal to the microprocessor controller module. As shown in FIG. 1, when the electrostatic protective module 10 is in the drive protection state, the electrostatic protective module 10 generates the electrostatic surge signal. In addition, according to driving status of the electrostatic protective module 10, the detection module 20 generates the driving record signal. As well, when the detection module 20 transmits the driving record signal to the microprocessor controller module 30, the microprocessor controller module 30 records the driving record signal.

Figure 6:
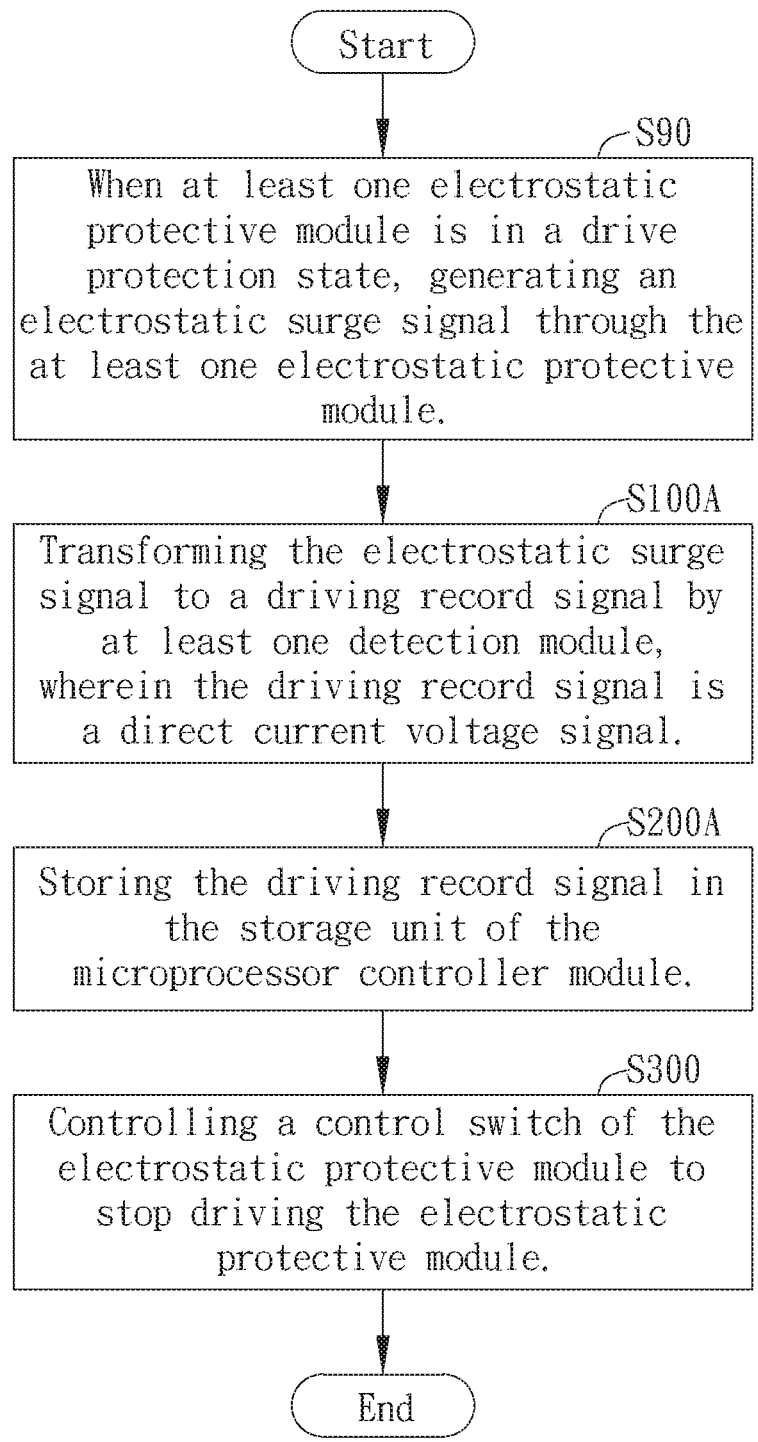
FIG. 6 is another flowchart diagram of the electrostatic detecting method.

FIG. 6 illustrates a flowchart of the electrostatic detecting method of the present invention. Aside from step S90 of FIG. 5, the electrostatic detecting method includes the following steps: step S100A, transforming the electrostatic surge signal by at least one detection module to the driving record signal, wherein the driving record signal is a direct current voltage signal; step S200A, storing the driving record signal with a storage unit of the microprocessor controller module; and step S300, controlling a control switch of the electrostatic protective module to stop driving protective module. As shown in FIGS. 3 and 4, the detection module 20 transforms the electrostatic surge signal to the driving record signal, wherein the driving record signal is a direct current voltage signal, and the storage module 310 of the microprocessor controller module 30 stores the driving record signal. In addition, the microprocessor controller module 30 controls the control switch 120 of the electrostatic protective module 10A to stop driving the electrostatic protective module 10A.

In comparison to conventional technology, the electrostatic protection circuit and the electrostatic detecting method of the present invention detects driving state of the electrostatic protective module through the electrostatic detection module, and outputs the driving record signal according to the driving status. In this manner, the protection positions and circuit paths of the protective circuit are recorded. It should be noted that the microprocessor controller module is able to read the driving record signal and build the electrostatic protection distribution map. In addition, in the electrostatic protection map, the electrostatic protective circuit can adjust the protection components of any block of electronic components in order to selectively turn on/off or adjust the level of electrostatic protection and accomplish the effect of electrostatic protection detection and verification.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

The invention claimed is:

1. An electrostatic detecting circuit, comprising:
   at least one electrostatic protective module;
   at least one detection module respectively connected to the at least one electrostatic protective module, wherein the at least one detection module generates a driving record signal according to a driving status of the at least one electrostatic protective module; and
   a microprocessor controller module coupled to the at least one detection module, wherein the microprocessor controller module records the driving record signal when the at least one detection module transmits the driving record signal to the microprocessor controller module;
   wherein a default state of the at least one electrostatic protective module is a stop protection state; when the at least one electrostatic protective module is driven, the at least one electrostatic protective module changes from the stop protection state to a drive protection state; the at least one electrostatic protective module generates an electrostatic surge signal when the at least one electrostatic protective is in the drive protection state, and the at least one detection module changes the electrostatic signal into the driving record signal, wherein the driving record signal is a direct voltage signal.

2. The electrostatic detecting circuit of claim 1, wherein each of the at least one electrostatic protective module further includes:
   a delay circuit having a protective resistor; and
   a control switch connected to the protective resistor in parallel, wherein the at least one electrostatic protective module stops the driving protection when the control switch turns on.

3. The electrostatic detecting circuit of claim 1, wherein the at least one detection module generates the driving record signal according to whether the status of the at least one electrostatic protective module has changed to the drive protection state.

4. The electrostatic detecting circuit of claim 1, wherein the microprocessor controller module includes:
   a storage unit storing the driving record signal;
   a read-in interface connected to the storage unit and acting as a transmission interface for the driving record signal.

5. The electrostatic detecting circuit of claim 3, wherein the microprocessor controller module stores and records the driving record signal.

6. The electrostatic detecting circuit of claim 1, wherein the at least one electrostatic protective module conducts an electrostatic current when the at least one electrostatic protective module is in the drive protection state.

7. The electrostatic detecting circuit of claim 4, further comprising:
   a verification distribution module connected to the read-in interface, wherein the verification distribution module reads the driving record signal and a position of each of the at least one electrostatic protective module to determine a protection distribution verification map.

8. An electrostatic detecting method, comprising:
   by at least one detection module, generating a driving record signal according to a driving state of at least one electrostatic protective module; wherein a default state of the at least one electrostatic protective module is a stop protection state, when the at least one electrostatic protective module is being driven, the at least one electrostatic protective module changes from the stop protection state to a drive protection state and generates an electrostatic surge signal; and through the at least one detection module, transforming the electrostatic surge signal into the driving record signal, wherein the driving record signal is a direct current voltage signal, and when transmitting the driving record signal to a microprocessor controller module, recording the driving record signal with the microprocessor controller module.

9. The electrostatic detecting method of claim 8, wherein the at least one detection module generates the driving record signal according to whether the at least one electrostatic protective module changes from the stop protection state to the drive protection state.

10. The electrostatic detecting method of claim 9, wherein the storing step of the microprocessor controller module comprises:

storing and recording the driving record signal through the microprocessor controller module.

11. The electrostatic detecting method of claim 8, wherein the storing step of the microprocessor controller module comprises:

storing the driving record signal through a storage unit of the microprocessor controller module.

12. The electrostatic detecting method of claim 8, further comprising:

controlling a control switch of the electrostatic protective module to stop driving the electrostatic protective module.

13. An electrostatic detecting circuit, comprising:

at least one electrostatic protective module, wherein each of the at least one electrostatic protective module further includes:

a delay circuit having a protective resistor; and a control switch connected to the protective resistor in parallel, wherein the at least one electrostatic protective module stops the driving protection when the control switch turns on;

at least one detection module respectively connected to the at least one electrostatic protective module, wherein the at least one detection module generates a driving record signal according to a driving status of the at least one electrostatic protective module; and a microprocessor controller module coupled to the at least one detection module, wherein the microprocessor controller module records the driving record signal when the at least one detection module transmits the driving record signal to the microprocessor controller module.

14. An electrostatic detecting circuit, comprising:

at least one electrostatic protective module;

at least one detection module respectively connected to the at least one electrostatic protective module, wherein the at least one detection module generates a driving record signal according to a driving status of the at least one electrostatic protective module; and a microprocessor controller module coupled to the at least one detection module, wherein the microprocessor controller module records the driving record signal when the at least one detection module transmits the driving record signal to the microprocessor controller module, the microprocessor controller module further includes:

a storage unit storing the driving record signal;

a read-in interface connected to the storage unit and acting as a transmission interface for the driving record signal; and a verification distribution module connected to the read-in interface, wherein the verification distribution module reads the driving record signal and a position of each of the at least one electrostatic protective module to determine a protection distribution verification map.

* * * * *